United States Patent
Bonn et al.

(10) Patent No.: US 11,844,497 B2
(45) Date of Patent: Dec. 19, 2023

(54) SYSTEMS AND METHODS FOR OBJECT MEASUREMENT IN MINIMALLY INVASIVE ROBOTIC SURGERY

(71) Applicant: Covidien LP, Mansfield, MA (US)

(72) Inventors: Kenlyn S. Bonn, Lakewood, CO (US); Dustin O. Slater, Frederick, CO (US); Justin Rogers, Meppershall (GB); James R. Fagan, Erie, CO (US); Anjali Dhiman, Commerce City, CO (US); John W. Linebarger, Lakewood, CO (US); Rayne Robertson, Firestone, CO (US); Keith W. Malang, Longmont, CO (US); Matthew Savary, Denver, CO (US); Joshua R. Snow, Clinton, CT (US); Tyler J. Bagrosky, Arvada, CO (US); Luciano Mazzaro, Boulder, CO (US); Jason M. Mucilli, Lakewood, CO (US); Dylan R. Kingsley, Broomfield, CO (US); Christopher V. Rainieri, Longmont, CO (US); Amanda H. Lennartz, Erie, CO (US); Alexandre Linhares Vieira, Sao Paulo (BR); Kent L. Howe, Peoria, AZ (US)

(73) Assignee: Covidien LP, Mansfield, MA (US)

( * ) Notice: Subject to any disclaimer, the term of this patent is extended or adjusted under 35 U.S.C. 154(b) by 302 days.

(21) Appl. No.: 17/168,259

(22) Filed: Feb. 5, 2021

(65) Prior Publication Data
US 2021/0267711 A1 Sep. 2, 2021

Related U.S. Application Data
(60) Provisional application No. 62/982,969, filed on Feb. 28, 2020.

(51) Int. Cl.
*A61B 1/00* (2006.01)
*A61B 90/00* (2016.01)
(Continued)

(52) U.S. Cl.
CPC ...... *A61B 1/0002* (2013.01); *A61B 1/000096* (2022.02); *A61B 90/06* (2016.02);
(Continued)

(58) Field of Classification Search
CPC . A61B 1/0002; A61B 1/000096; A61B 90/06; A61B 90/30; A61B 90/361;
(Continued)

(56) References Cited

U.S. PATENT DOCUMENTS

2013/0308827 A1* 11/2013 Dillavou .............. G06T 11/00
382/107
2017/0165013 A1* 6/2017 Itkowitz .............. A61B 34/35
(Continued)

FOREIGN PATENT DOCUMENTS

WO 2015149041 A1 10/2015
WO 2020028202 A1 2/2020

OTHER PUBLICATIONS

International Search Report dated Aug. 6, 2021 and Written Opinion completed May 25, 2021 corresponding to counterpart Int'l Patent Application.
(Continued)

*Primary Examiner* — Anh Tuan T Nguyen
*Assistant Examiner* — Sung Ham
(74) *Attorney, Agent, or Firm* — Carter, DeLuca & Farrell LLP (57) ABSTRACT

A computer-implemented method of object enhancement in endoscopy images includes capturing an image of an object within a surgical operative site via an imaging device, determining a size of the object based on the captured image
(Continued)

of the object, displaying the captured image of the object, and displaying on the displayed captured image of the object a representation of the determined size of the object.

20 Claims, 4 Drawing Sheets (51) Int. Cl.
  *A61B 90/30* (2016.01)
  *A61B 34/30* (2016.01)
(52) U.S. Cl.
  CPC ............ *A61B 90/30* (2016.02); *A61B 90/361* (2016.02); *A61B 90/37* (2016.02); *A61B 34/30* (2016.02)
(58) Field of Classification Search
  CPC . A61B 90/37; A61B 34/30; A61B 2034/2051; A61B 2034/2053; A61B 2034/2055; A61B 2090/3937; A61B 34/37; A61B 90/96; A61B 2090/061; A61B 2090/364; A61B 2034/2065; G06T 2207/10152; G06T 2207/30004; G06T 7/62; G06T 2207/10068; G06T 2207/20101
  See application file for complete search history.

(56) References Cited

U.S. PATENT DOCUMENTS

| | | | |
|---|---|---|---|
| 2018/0053300 A1* | 2/2018 | Podilchuk | G06T 7/0016 |
| 2018/0174318 A1* | 6/2018 | Wang | H04N 23/56 |
| 2018/0192982 A1* | 7/2018 | Pereira | G06T 11/60 |
| 2019/0058836 A1 | 2/2019 | Lee et al. | |
| 2019/0175009 A1 | 6/2019 | Mintz et al. | |
| 2019/0192237 A1 | 6/2019 | Harrah et al. | |
| 2019/0328349 A1 | 10/2019 | Pereira et al. | |
| 2020/0163731 A1* | 5/2020 | Itkowitz | A61B 1/00193 |
| 2021/0030497 A1* | 2/2021 | Daley | A61B 90/361 |
| 2021/0093227 A1* | 4/2021 | Hitaka | G06T 7/62 |
| 2021/0177526 A1* | 6/2021 | Goyette | A61B 34/20 |
| 2022/0211460 A1* | 7/2022 | Tabandeh | A61B 34/70 |

OTHER PUBLICATIONS

International Preliminary Report and Written Opinion dated Sep. 9, 2022 corresponding to counterpart Int'l Patent Application PCT/US2021/018200.

* cited by examiner

SYSTEMS AND METHODS FOR OBJECT MEASUREMENT IN MINIMALLY INVASIVE ROBOTIC SURGERY

CROSS-REFERENCE TO RELATED APPLICATIONS

The present application claims the benefit of and priority to U.S. Provisional Patent Application Ser. No. 62/982,969, filed on Feb. 28, 2020, the entire content of which being hereby incorporated by reference.

FIELD

The disclosure relates to robotics, and more specifically to robotic surgical devices, assemblies, and/or systems for performing endoscopic surgical procedures and methods of use thereof.

BACKGROUND

Endoscopic instruments have become widely used by surgeons in endoscopic surgical procedures because they enable surgery to be less invasive as compared to conventional open surgical procedures in which the surgeon is required to cut open large areas of body tissue. As a direct result thereof, endoscopic surgery minimizes trauma to the patient and reduces patient recovery time and hospital costs.

Some endoscopic instruments incorporate rotation and/or articulation features, thus enabling rotation and/or articulation of an end effector assembly of the endoscopic surgical instrument, disposed within the surgical site, relative to a handle assembly of the endoscopic surgical instrument, which remains externally disposed, to better position the end effector assembly for performing a surgical task within the surgical site. An endoscopic camera communicating with an operating room display is also often utilized in endoscopic surgery to enable the surgeon to visualize the surgical site as the end effector assembly is maneuvered into position and operated to perform the desired surgical task.

SUMMARY

The disclosure relates to devices, systems, and methods for surgical instrument identification in images. In accordance with aspects of the disclosure, a system for measuring an object in a surgical site is presented. The system includes an imaging device and an imaging device control unit. The imaging device control unit includes a processor and a memory storing instructions. The instructions, when executed by the processor, cause the system to: capture an image of an object within a surgical operative site via the imaging device; display the captured image of the object; and display, on the displayed captured image of the object, a representation of the determined size of the object.

In an aspect of the present disclosure, the processor may be configured to determine the size of the object based on a depth of each of a plurality of pixels in the captured image, a focal length of the imaging device, and a field of view of the imaging device.

In another aspect of the present disclosure, the processor may be further configured to determine the size of the object based on: a geometry of a surgical instrument captured in the image; a depth of each of a plurality of pixels in the captured image; a first location of the surgical instrument in a first frame of the captured image; a second location of the surgical instrument in a second frame of the captured image; and a difference between the first location and the second location.

In an aspect of the present disclosure, the processor may be configured to determine the size of the object by providing, as input to a trained neural network stored in the memory: a depth of each of a plurality of pixels in the captured image; a focal length of the imaging device; and a field of view of the imaging device.

In yet another aspect of the present disclosure, the system may further include a light source configured to emit structured light within the surgical operative site.

In a further aspect of the present disclosure, the instructions, when executed, may further cause the system to: capture an image of a surgical instrument within the surgical operative site by the imaging device; and determine a location of the surgical instrument within a field of view of the captured image of the surgical instrument based on the structured light.

In yet a further aspect of the present disclosure, the instructions, when executed, may further cause the system to re-center the imaging device based on the determined location of the surgical instrument; generate a re-centered image based on the re-centered imaging device; and display the re-centered image on the display.

In an aspect of the present disclosure, the processor may be further configured to provide a visual warning and/or audio warning when the object is disposed outside of a field of view of the captured image.

In a further aspect of the present disclosure, the object may be a surgical instrument.

In yet another aspect of the present disclosure, the object may be a surgical instrument, and the processor may be configured to disable the surgical instrument when the surgical instrument is outside of a field of view of the captured image.

In a further aspect of the present disclosure, the instructions, when executed, may further cause the system to highlight the surgical instrument on the display when the surgical instrument is in the field of view of the captured image.

In accordance with aspects of the disclosure, a computer-implemented method for measuring an object in a surgical site is presented. The method includes capturing an image of an object within a surgical operative site by an imaging device; determining a size of the object based on the captured image of the object; displaying the captured image of the object; and displaying, on the displayed captured image of the object, a representation of the determined size of the object.

In yet a further aspect of the present disclosure, the method may determine the size of the object based on a depth of each of a plurality of pixels in the captured image, a focal length of the imaging device, and a field of view of the imaging device.

In yet another aspect of the present disclosure, the method may determine the size of the object based on: a geometry of a surgical instrument captured in the image; a depth of each of a plurality of pixels in the captured image; a first location of the surgical instrument in a first frame of the captured image; a second location of the surgical instrument in a second frame of the captured image; and a difference between the first location and the second location.

In a further aspect of the present disclosure, the method may determine the size of the object by providing, as input to a trained neural network: a depth of each of a plurality of pixels in the captured image; a focal length of the imaging device; and a field of view of the imaging device.

In yet a further aspect of the present disclosure, the method may further include emitting structured light within the surgical operative site.

In yet another aspect of the present disclosure, the method may further include: capturing an image of a surgical instrument within the surgical operative site by the imaging device and determining a location of the surgical instrument within a field of view of the captured image of the surgical instrument based on the structured light.

In a further aspect of the present disclosure, the method may further include: re-centering the imaging device based on the determined location of the surgical instrument; generating a re-centered image based on the re-centered imaging device; and displaying on the display the re-centered image.

In an aspect of the present disclosure, the method may further include providing a visual warning, audio warning, and/or a tactile warning when the object is disposed outside of a field of view of the captured image.

In accordance with the present disclosure, a non-transitory storage medium is provided that stores a program, which causes a computer to execute a computer-implemented method for measuring an object in a surgical site. The computer-implemented method includes capturing an image of an object within a surgical operative site by an imaging device and determining a size of the object based on the captured image of the object. The size of the objected is determined based on: a depth of each of a plurality of pixels in the captured image; a focal length of the imaging device; and/or a field of view of the imaging device. The computer-implemented method further includes displaying the captured image of the object; and displaying, on the displayed captured image of the object, a representation of the determined size of the object.

Further details and aspects of various embodiments of the disclosure are described in more detail below with reference to the appended figures.

BRIEF DESCRIPTION OF THE DRAWINGS

Embodiments of the disclosure are described herein with reference to the accompanying drawings, wherein.

Further details and aspects of exemplary embodiments of the disclosure are described in more detail below with reference to the appended figures. Any of the above aspects and embodiments of the disclosure may be combined without departing from the scope of the disclosure.

DETAILED DESCRIPTION

Embodiments of the presently disclosed devices, systems, and methods of treatment are described in detail with reference to the drawings, in which like reference numerals designate identical or corresponding elements in each of the several views. As used herein, the term "distal" refers to that portion of a structure that is farther from a user, while the term "proximal" refers to that portion of a structure that is closer to the user. The term "clinician" refers to a doctor, nurse, or other care provider and may include support personnel.

The disclosure is applicable where images of a surgical site are captured. Endoscope systems are provided as an example, but it will be understood that such description is exemplary and does not limit the scope and applicability of the disclosure to other systems and procedures. It is contemplated that the disclosure is applicable to, for example, robotic surgical systems as well as laproscopic, hand-operated surgery.

Figure 1:
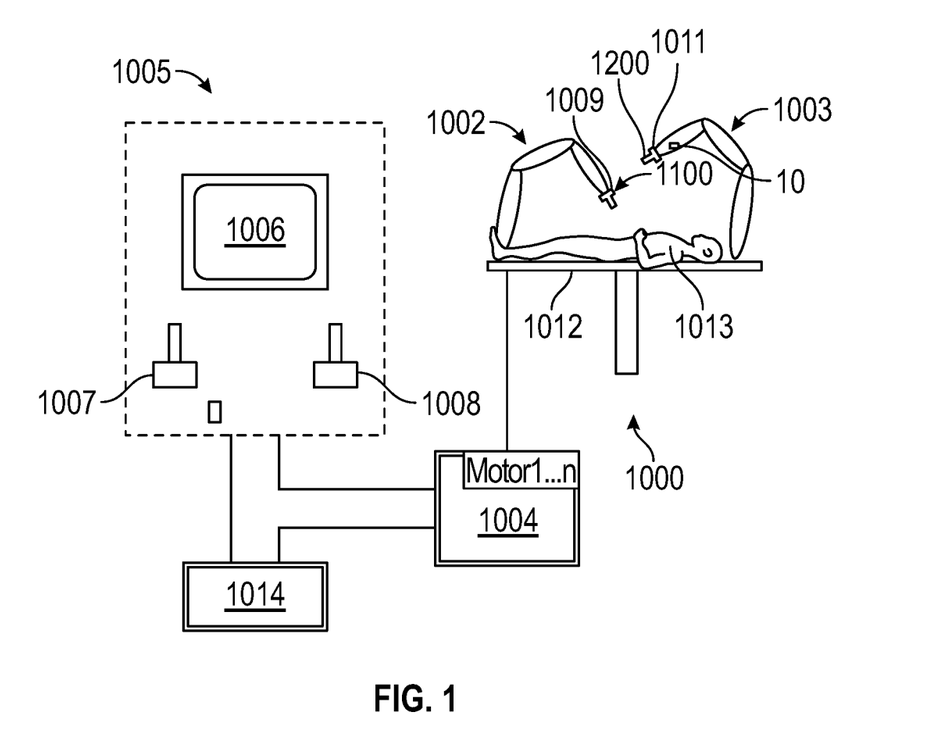
FIG. 1 is a schematic diagram of a robotic surgical system provided in accordance with aspects of the present disclosure.

With reference to FIG. 1, a robotic surgical system exemplifying the aspects and features of the present disclosure is shown identified by reference numeral 1000. Robotic surgical system 1000 includes a plurality of robot arms 1002, 1003; a control device 1004; an operating console 1005 coupled with control device 1004; and an endoscope system 10 coupled to the robot arm 1003. In aspects, the endoscope system 10 may be independent of the robot arm 1003. Operating console 1005 may include a display device 1006, which may be set up in particular to display three-dimensional images; and manual input devices 1007, 1008, to enable a clinician to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014 coupled to control device 1004, in which pre-operative data from patient 1013 and/or anatomical atlases are stored.

Each of the robot arms 1002, 1003 may include a plurality of segments, which are connected through joints, and an attaching device 1009, 1011, to which may be attached, for example, an end effector assembly 1100, 1200, respectively. End effector assembly 1200 may be any suitable end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Manual input devices 1007, 1008 of robotic surgical system 1000 may further include a motion activation control, a motion-sensing assembly including a motor, rotation and/or articulation lockout features, excessive torque limiting features, and/or a rotation control, similarly as detailed above, to provide the user with the ability to control manipulation of end effector assemblies 1100, 1200, by moving manual input devices 1007, 1008 relative to a reference position.

Figure 2:
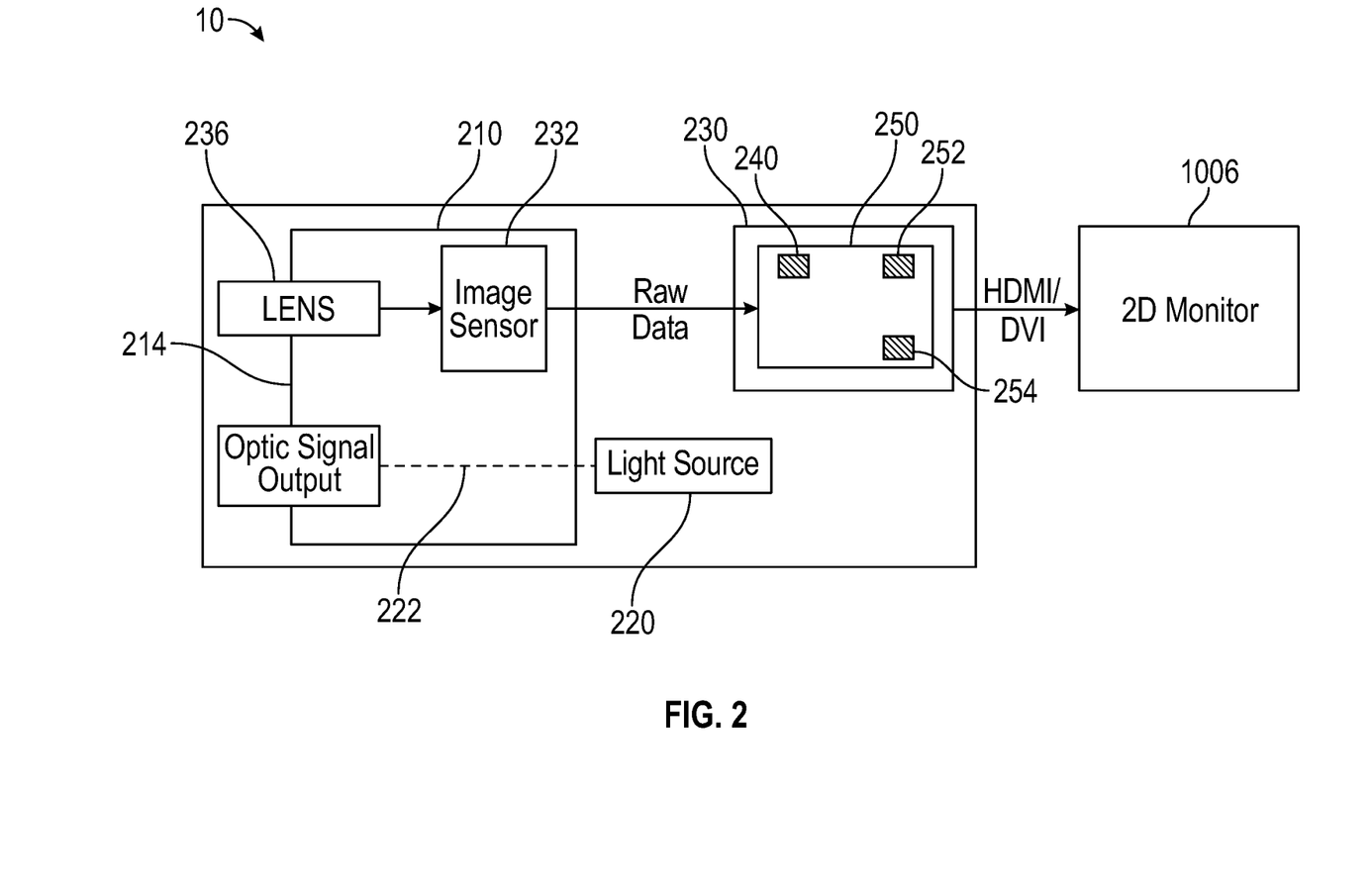
FIG. 2 is a schematic diagram of a visualization system for use in the robotic surgical system of FIG. 1.

Referring to FIG. 2, there is shown a schematic illustration of a visualization system, such as, for example, the endoscope system 10 of the robotic surgical system 1000 shown in FIG. 1. The endoscope system 10 may be coupled to one of the robot arms (e.g., robot arm 1003) or incorporated into the end effector assembly 1200. In other aspects, the endoscope system 10 may be a stand-alone system that is independently movable relative to the robot arms 1002, 1003. The endoscope system 10 generally includes an imaging device 210 (e.g., a camera), a light source 220, a video system 230, and a display 1006. The light source 220 is configured to provide light to a surgical site via a fiber guide 222 of the imaging device 210. The imaging device 210 has a distal end portion 214 including an objective lens 236 for capturing the image at the surgical site. The objective lens 236 forwards the image to an image sensor 232 of the imaging device 210. The image is then communicated from the imaging device 210 to the video system 230 for processing.

The video system 230 includes an imaging device control unit 250 for controlling the endoscope system 10 and processing images. The imaging device control unit 250 includes a processor 252 connected to a computer-readable storage medium or a memory 254 which may be a volatile type memory, such as RAM, or a non-volatile type memory, such as flash media, disk media, or other types of memory. In various embodiments, the processor 252 may be another type of processor such as, without limitation, a digital signal processor, a microprocessor, an ASIC, a graphics processing unit (GPU), field-programmable gate array (FPGA), or a central processing unit (CPU). It is contemplated that the processor 252 can be separate from the imaging device control unit 250 and can communicate with the device control unit 250 through communication buses of a circuit board and/or through communication cables such as serial ATA cables or other types of cables, and/or wirelessly (e.g., via Bluetooth and/or Wi-Fi).

In various embodiments, the memory 254 can be random access memory, read-only memory, magnetic disk memory, solid-state memory, optical disc memory, and/or another type of memory. In various embodiments, the memory 254 can be separate from the imaging device control unit 250 and can communicate with the processor 252 through communication buses of a circuit board and/or through communication cables such as serial ATA cables or other types of cables. The memory 254 includes computer-readable instructions that are executable by the processor 252 to operate the imaging device control unit 250. In various embodiments, the imaging device control unit 250 may include a network interface 240 to communicate with other computers or a server.

In machine learning, a convolutional neural network (CNN) is a class of artificial neural network (ANN), most commonly applied to analyzing visual imagery. The convolutional aspect of a CNN relates to applying matrix processing operations to localized portions of an image, and the results of those operations (which can involve dozens of different parallel and serial calculations) are sets of many features that are used to train neural networks. A CNN typically includes convolution layers, activation function layers, and pooling (typically max pooling) layers to reduce dimensionality without losing too many features. Additional information may be included in the operations that generate these features. Providing unique information that yields features that give the neural networks information can be used to ultimately provide an aggregate way to differentiate between different data input to the neural networks.

The flow diagrams of FIGS. 3-5 described below include various blocks described in an ordered sequence. However, those skilled in the art will appreciate that one or more blocks of the flow diagram may be performed in a different order, repeated, and/or omitted without departing from the scope of the disclosure. The below description of the flow diagram refers to various actions or tasks performed by the video system 230, but those skilled in the art will appreciate that the video system 230 is exemplary. In various embodiments, the disclosed operations can be performed by another component, device, or system. In various embodiments, the video system 230 or other component/device performs the actions or tasks via one or more software applications executing on the processor 252. In various embodiments, at least some of the operations can be implemented by firmware, programmable logic devices, and/or hardware circuitry. Other implementations are contemplated to be within the scope of the disclosure.

Figure 3:
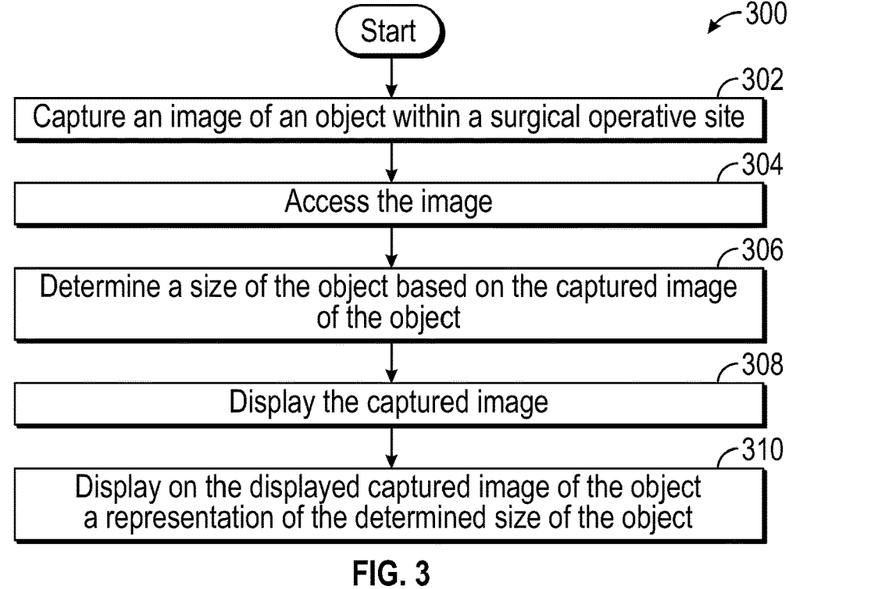
FIG. 3 is a flowchart illustrating a method for object enhancement in endoscopy images in accordance with an exemplary embodiment of the disclosure.

Referring now to FIG. 3, there is shown an operation 300 for object enhancement in endoscopy images, such as, for example, measuring the size of tissue (e.g., organs) during a surgical procedure using a camera. In various embodiments, the operation 300 can be performed by the endoscope system 10 described above. In various embodiments, the operation 300 can be performed by another type of system and/or during another type of procedure.

Initially, at step 302, an image of a surgical site is captured via the objective lens 236 of the imaging device 210 and forwarded to the image sensor 232. The term "image" as used herein may include still images or moving images (e.g., video) including a plurality of pixels. The captured image is communicated to the video system 230 for processing. When the image is captured, it may include objects, such as tissue (e.g., an organ) and the end effector assembly 1100 (FIG. 1) treating the tissue.

At step 304, the video system 230 accesses the image for further processing, and at step 306, the video system 230 determines the size of an object in the captured image. To determine the size of the object (e.g., the size of the organ) in the captured image, the video system 230 accesses data relating to depth information about each of the pixels in the captured image, data relating to a focal length of the imaging device 210, and data relating to a field of view of the imaging device 210. The image includes a stereographic image having a left image and a right image, and the video system 230 may calculate depth information based on determining a horizontal disparity mismatch between the left image and the right image. In various embodiments, the depth information may include pixel depth. The video system 230 determines the object size based on the depth information, the field of view, and the focal length. For example, the video system 230 may use basic trigonometry to determine the size of the object based on the relationship between the depth information, the field of view, and the focal length. In various embodiments, the video system 230 may use color, reflection, and/or refraction to determine the size of the object.

The video system 230 inputs the depth information, the focal length, and the field of view to the neural network stored in memory 254. The depth information now associated with the pixels can be input to the image processing path to feed the neural network. At this point, the neural networks may start with various mathematical operations predicting the object size and/or object type. It is contemplated that the extraction of depth does not need to be real-time for training the neural networks.

The neural network is trained based on tagging objects in training images, and wherein the training further includes augmenting the training images to include adding noise, changing colors, hiding portions of the training images, scaling of the training images, rotating the training images, and/or stretching the training images. In various embodiments, the training includes supervised, unsupervised, and/or reinforcement learning. It is contemplated that the training may be performed by a processor external to the video system 230.

At step 308, the video system 230 displays the object of the captured image on the display 1006 (FIG. 2). At step 310, the video system 230 displays on the displayed captured image a representation of the determined size of the object in the captured image. In various embodiments, the object may include structures and/or organs. In aspects, the representation of the determined size includes a visual marker indicating measurement dimensions. For example, if the endoscope system 10 determines that the organ has a diameter of 30 mm, then the display 1006 may display a value of 30 mm adjacent to the image of the organ. In aspects, the representation of the determined size of the object may be overlaid on the displayed captured image of the object.

In another embodiment, the captured image may be a video that includes a first frame and a second frame. The first frame may include an image of a particular portion (e.g., a tip and/or distal portion) of the end effector assembly 1100 at a first location in the surgical site, and the second frame may include an image of the same portion of the end effector assembly 1100 as in the first frame but at a second location in the surgical site. To assist in determining the size of the object (e.g., organ) in the captured image, the video system 230 accesses data relating to a geometry of a surgical instrument (e.g., tip size) and data relating to depth information about each of the pixels in the captured image. In particular, the video system 230 determines the first location of the tip of the end effector assembly 1100 in the first frame and determines the second location of the tip of the end effector assembly 1100 in the second frame. The video system 230 calculates a reference value based on a difference between the first location and the second location and determines the size of the object in the captured image based on the reference value and pixel depth information. The endoscope system 10 is configured to determine a distance between the first and second locations.

Figure 4:
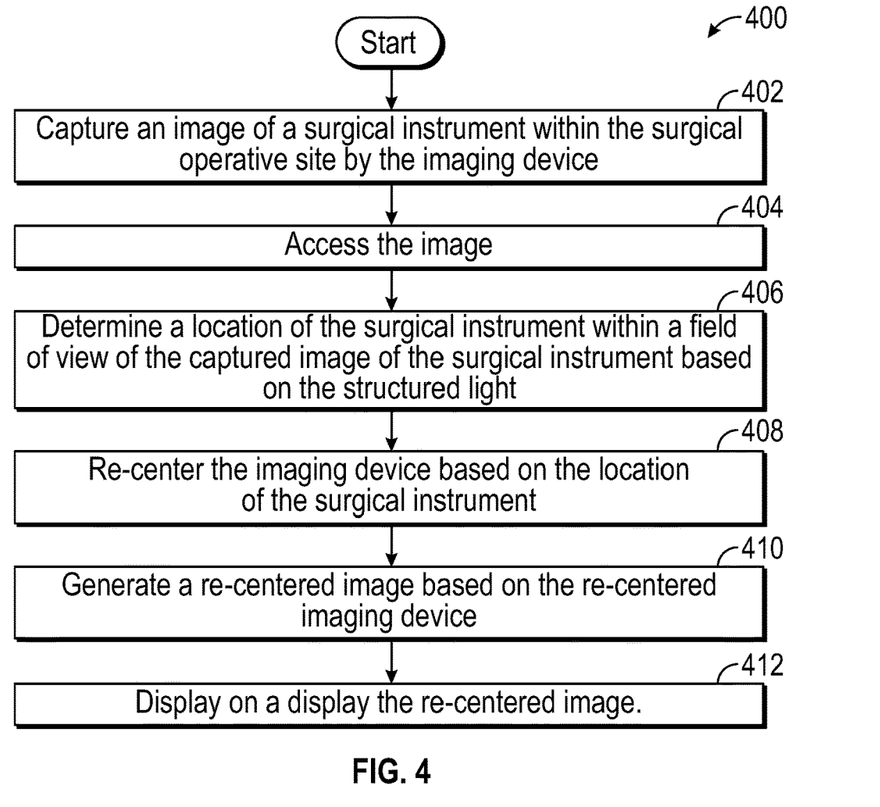
FIG. 4 is a flowchart illustrating a method for object enhancement in endoscopy images in accordance with another exemplary embodiment of the disclosure.

Referring now to FIG. 4, there is shown another exemplary operation 400 for object measurement in endoscopy images performed by the endoscope system 10. Initially, at step 402, the video system 230 captures an image of the end effector assembly 1100 within the surgical operative site. The end effector assembly 1100 may include a landmark (not explicitly shown) configured to reflect the structured light emitted by the light source 220 (FIG. 2) of the endoscope system 10 such that the captured image includes the reflected structured light. Structured light is the process of projecting a known pattern (often grids or horizontal bars) on to a scene. The way that these known patterns deform when striking surfaces allows imaging systems to calculate the depth and surface information of the objects in the scene. In various embodiments, the landmark may include, for example, a geometric shape, a barcode, or alphanumeric characters.

At step 404, the video system 230 accesses the image, and at step 406, the video system 230 determines the location of the end effector assembly 1100 within a field of view (FOV) of the imaging device 210 based on the reflected structured light.

At step 408, the video system 230 re-centers the imaging device 210 based on the location of the end effector assembly 1100 determined in step 406, such that the imaging device 210 maintains its lens 236 directed at the end effector assembly 1100 as the end effector assembly 1100 moves within the surgical site. At step 410, the video system 230 generates a re-centered image of the end effector assembly 1100 within the surgical operative site. At step 412, the re-centered image is displayed on the display 1006. For example, the re-centering of the image based on the location of the end effector assembly 1100 would operate like a so-called "camera follow-me" mode.

In various embodiments, the end effector assembly 1100 may include a device ID. The device ID may be associated with additional device parameters such as type of device, serial number, and other relevant information. In various embodiments, the video system 230 may provide a visual warning and/or audio warning when the object is disposed outside of a field of view of the captured image based on the device ID.

In a case where the end effector assembly 1100 moves outside of the FOV of the imaging device 210, the video system 230 may be configured to alert the clinician using an audible warning (e.g., a beep) or a visual warning (e.g., highlighting the display 1006 red). In various embodiments, tactile (e.g., vibration) warnings may be used to alert the clinician. When the end effector assembly 1100 moves outside of the FOV, the video system 230 may be configured to disable the end effector assembly 1100 to prohibit a clinician from activating the end effector assembly 1100. The video system 230 may be configured to highlight the displayed end effector assembly 1100, such that the end effector assembly 1100 is shown on the display 1006 in a more visible color relative to the rest of the displayed image.

Figure 5:
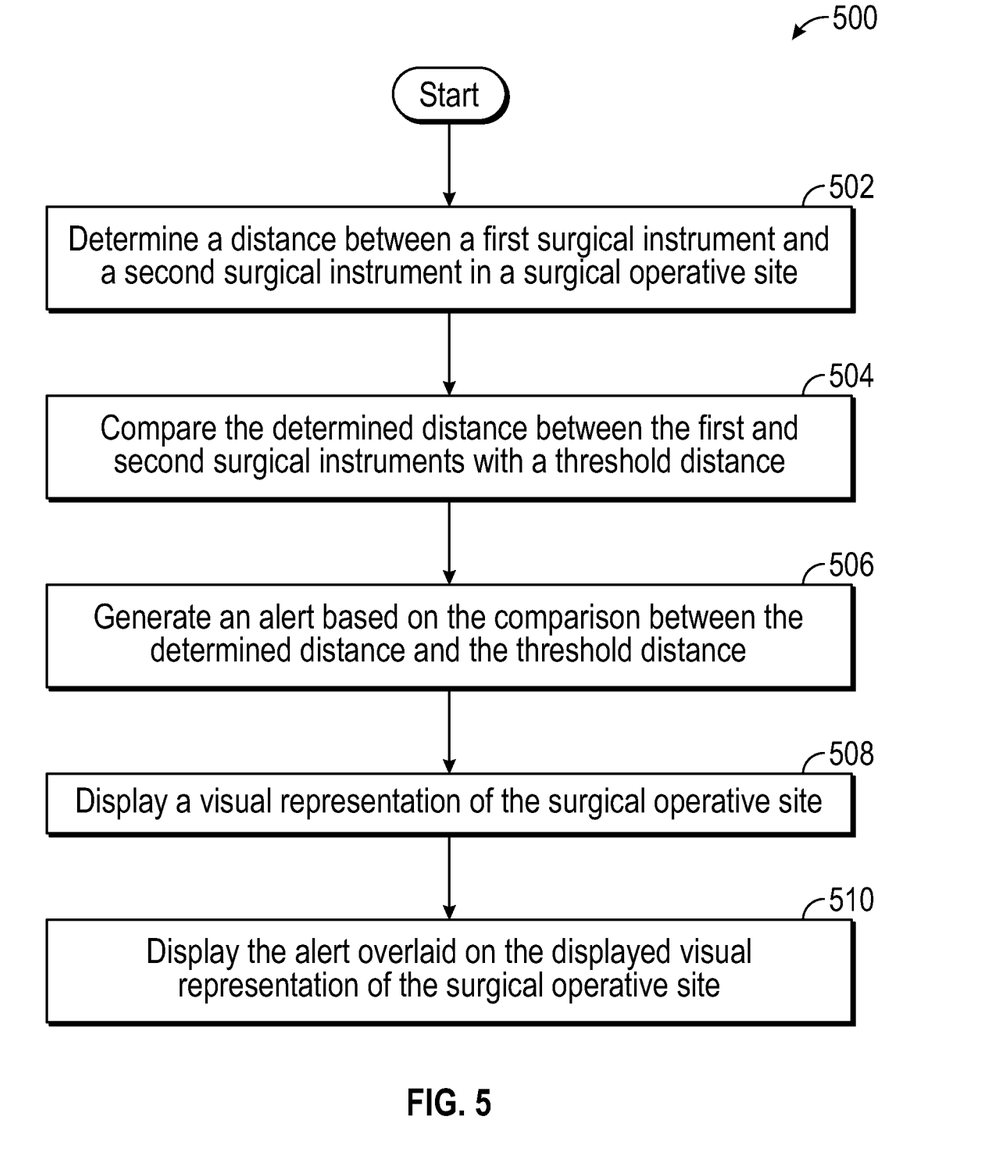
FIG. 5 is a flowchart illustrating a method for presence of a surgical instrument during robotic surgery in accordance with an exemplary embodiment of the disclosure.

Referring now to FIG. 5, there is shown another exemplary method for performing robotic surgery. During some robotic surgical procedures, non-robotic surgical instruments may be used alongside robotically-operated surgical instruments. Accordingly, it may be useful to improve the coordination between the robotic and non-robotic surgical instruments by detecting the presence of the non-robotically operated surgical instruments. It is useful for the clinician to be alerted to the presence and/or proximity of any non-robotic surgical instruments being operated by a user (e.g., an assisting surgeon, or a physician assistant).

Initially, at step 502, the control device 1004 of the robotic surgical system 1000 determines a distance between a first surgical instrument such as, for example, the end effector assembly 1100 (FIG. 1), and a second surgical instrument (not shown) within the surgical operative site. The end effector assembly 1100 may be equipped with a sensor, such as, for example, an RF sensor or an optical sensor configured to detect the proximity of objects (e.g., the second surgical instrument or a critical structure). In aspects, the sensor may be included in a so-called "chip-on-a-tip" attachment for the end effector assembly 1100. In various embodiments, the control device 1004 determines a location of the first surgical instrument relative to the second surgical instrument based on the first sensor. For example, the video system 230 may determine a location of the end effector assembly 1100 relative to the second surgical instrument (e.g., a second end effector assembly) based on feedback received from the sensor.

At step 504, the control device 1004 compares the determined distance between the first and second surgical instruments with a threshold distance. The threshold distance is a predetermined distance that is considered a safe or acceptable distance that poses little risk that the second surgical instrument will collide with the first surgical instrument. For example, the threshold distance may be about 4 inches or more. In some aspects, the threshold distance may be manually input by a clinician.

At step 506, the control device 1004 generates an alert based on the comparison between the determined distance and the threshold distance. For example, the control device 1004 may generate an audio or visual alert when the first surgical instrument is at or within the threshold distance from the second surgical instrument or a critical structure. In various embodiments, the alert may include a visual alert (e.g., a text overlay and/or a flashing light) and/or an audio alert indicating that the second surgical instrument is too close to the first surgical instrument. In various embodiments, the control device 1004 may terminate activation and/or movement of at least one of the first or second surgical instruments when the determined distance is at or within the threshold distance.

At step 508, the video system 230 displays a visual representation of the surgical operative site on the display 1006 (FIG. 2). The visual representation of the surgical site displayed on the display 1006 includes a visual representation of the first and second surgical instruments and the tissue being operated on. In various embodiments, the video system 230 may capture an image of the surgical operative site using an imaging device 10. The determined distance may be displayed in proximity to the visual representation of the first and/or second surgical instruments on the display 1006.

At step 510, the video system 230 displays the alert overlaid on the displayed visual representation of the surgical operative site. The alert may be a visual warning, including a changing of the color of the displayed first surgical instrument or the displayed second surgical instrument and/or displaying a flashing light on the display 1006. In one embodiment, the alert may include rendering the second surgical instrument visible on the display 1006 upon the second surgical instrument moving to a position within the threshold distance from the first surgical instrument.

In various embodiments, the video system 230 may capture an image within the surgical operative site via an imaging device. For example, the image may be from a perspective of a second surgical instrument (e.g., an endoscope) different than the end effector assembly 1100. The video system 230 accesses the image and displays the image on a display (not shown). In various embodiments, the display may include a tablet, a mobile device, a sub-window displayed on the display 1006, and/or an AR/VR device. For example, a clinician assisting a surgeon during robotic surgery may be wearing AR/VR goggles and would be able to see from the angle of their surgical instrument when they are in close proximity to the end effector assembly 1100.

In various embodiments, the video system 230 may determine tracking information for the second surgical instrument based on a sensor disposed on the second surgical instrument. In various embodiments, the video system 230 may display the tracking information of the second surgical instrument on the display 1006. In various embodiments, the video system 230 may use the tracking information to track the trajectory or path of the first and second surgical instruments for optimizing surgical steps.

The phrases "in an embodiment," "in embodiments," "in some embodiments," or "in other embodiments" may each refer to one or more of the same or different embodiments in accordance with the disclosure. A phrase in the form "A or B" means "(A), (B), or (A and B)." A phrase in the form "at least one of A, B, or C" means "(A); (B); (C); (A and B); (A and C); (B and C); or (A, B, and C)." The term "clinician" may refer to a clinician or any medical professional, such as a doctor, nurse, technician, medical assistant, or the like, performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms, or codes may be converted or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms, or codes may be contained on one or more machine-readable media or memory. The term "memory" may include a mechanism that provides (for example, stores and/or transmits) information in a form readable by a machine such as a processor, computer, or a digital processing device. For example, a memory may include read-only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the disclosure. Various alternatives and modifications can be devised by those skilled in the art without departing from the disclosure. Accordingly, the disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A system for measuring an object in a surgical site, comprising:
   an imaging device configured to capture an image of an object within a surgical operative site; and
   an imaging device control unit configured to control the imaging device, the imaging device control unit including:
      a processor; and
      a memory storing instructions which, when executed by the processor, cause the system to:
         capture an image of an object within a surgical operative site via the imaging device;
         determine a size of the object based on:
            a geometry of a surgical instrument captured in the captured image;
            a depth of each of a plurality of pixels in the captured image;
            a first location of the surgical instrument in a first frame of the captured image;
            a second location of the surgical instrument in a second frame of the captured image; and
            a difference between the first location and the second location;
         display the captured image of the object; and
         display, on the displayed captured image of the object, a representation of the determined size of the object.

2. The system of claim 1, wherein the processor is configured to determine the size of the object by providing, as input to a trained neural network stored in the memory:
   a depth of each of a plurality of pixels in the captured image;
   a focal length of the imaging device; and
   a field of view of the imaging device.

3. The system of claim 1, further comprising a light source configured to emit structured light within the surgical operative site.

4. The system of claim 3, wherein the instructions, when executed, further cause the system to:
   capture an image of the surgical instrument within the surgical operative site by the imaging device; and
   determine a location of the surgical instrument within a field of view of the captured image of the surgical instrument based on the structured light.

5. The system according to claim 4, wherein the instructions, when executed, further cause the system to:
   re-center the imaging device based on the determined location of the surgical instrument;
   generate a re-centered image based on the re-centered imaging device; and
   display the re-centered image on the display.

6. The system of claim 1, wherein the processor is configured to provide at least one of a visual warning or an audio warning when the surgical instrument is disposed outside of a field of view of the captured image.

7. The system of claim 1, wherein the processor is configured to disable the surgical instrument when the surgical instrument is outside of a field of view of the captured image.

8. The system of claim 7, wherein the instructions, when executed, further cause the system to highlight the surgical instrument on the display when the surgical instrument is in the field of view of the captured image.

9. The system of claim 1, wherein the instructions, when executed, further cause the system to:
   determine a distance between the first and second locations; and
   calculate a reference value based on the distance between the first and second locations.

10. The system of claim 9, wherein determining the size of the object is further based on the reference value.

11. A computer-implemented method for measuring an object in a surgical site, comprising:
    capturing an image of an object within a surgical operative site via an imaging device;
    determining a size of the object based on:
       a geometry of a surgical instrument captured in the captured image;
       a depth of each of a plurality of pixels in the captured image;
       a first location of the surgical instrument in a first frame of the captured image;
       a second location of the surgical instrument in a second frame of the captured image; and
       a difference between the first location and the second location;
    displaying the captured image of the object; and
    displaying, on the displayed captured image of the object, a representation of the determined size of the object.

12. The computer-implemented method of claim 11, further comprising determining the size of the object by providing, as input to a trained neural network:
    a depth of each of a plurality of pixels in the captured image;
    a focal length of the imaging device; and
    a field of view of the imaging device.

13. The computer-implemented method of claim 11, further comprising emitting structured light within the surgical operative site.

14. The computer-implemented method of claim 13, further comprising:
    capturing an image of the surgical instrument within the surgical operative site via the imaging device; and
    determining a location of the surgical instrument within a field of view of the captured image of the surgical instrument based on the structured light.

15. The computer-implemented method of claim 14, further comprising:
    re-centering the imaging device based on the determined location of the surgical instrument;
    generating a re-centered image based on the re-centered imaging device; and
    displaying the re-centered image on the display.

16. The computer-implemented method of claim 11, further comprising providing at least one of a visual warning, an audio warning, or a tactile warning when the surgical instrument is disposed outside of a field of view of the captured image.

17. The computer-implemented method of claim 11, further comprising:
    determining a distance between the first and second locations; and
    calculating a reference value based on the distance between the first and second locations.

18. The computer-implemented method of claim 17, wherein determining the size of the object is further based on the reference value.

19. A non-transitory storage medium that stores a program causing a computer to execute a computer-implemented method for measuring an object in a surgical site, the computer-implemented method comprising:

capturing an image of an object within a surgical operative site via an imaging device;
determining a size of the object based on:
- a geometry of a surgical instrument captured in the captured image;
- a depth of each of a plurality of pixels in the captured image;
- a first location of the surgical instrument in a first frame of the captured image;
- a second location of the surgical instrument in a second frame of the captured image; and
- a difference between the first location and the second location;

displaying the captured image of the object; and
displaying, on the displayed captured image of the object, a representation of the determined size of the object.

20. The non-transitory storage medium of claim 19, wherein the computer-implemented method further comprises calculating a reference value based on a distance between the first and second locations, and determining the size of the object is further based on the reference value.

* * * * *